United States Patent [19]

Goldstein

[11] Patent Number: 4,594,135

[45] Date of Patent: Jun. 10, 1986

[54] PROCESS AND APPARATUS FOR ELECTRICALLY DESORBING COMPONENTS SELECTIVELY SORBED ON GRANULES

[75] Inventor: Arthur L. Goldstein, Weston, Mass.

[73] Assignee: Ionics Incorporated, Watertown, Mass.

[21] Appl. No.: 703,581

[22] Filed: Feb. 20, 1985

[51] Int. Cl.[4] ............................................. C07K 3/18
[52] U.S. Cl. .................................. 204/180.1; 204/301; 204/182.3
[58] Field of Search ............... 204/151, 180 R, 180 P, 204/301

[56] References Cited

U.S. PATENT DOCUMENTS

| | | | |
|---|---|---|---|
| 3,450,630 | 6/1969 | Bloch et al. | 210/644 |
| 3,839,162 | 10/1974 | Ammer | 204/263 |
| 3,846,270 | 11/1974 | Muto et al. | 204/263 |
| 3,847,788 | 11/1974 | Wallace | 204/301 |
| 4,400,250 | 8/1983 | Fairhurst | 204/151 |
| 4,484,989 | 11/1984 | Mansell | 204/296 |

FOREIGN PATENT DOCUMENTS

| | | | |
|---|---|---|---|
| 1387457 | 6/1964 | France | 204/180 P |
| 0128584 | 11/1978 | Japan | 204/180 P |
| 0126679 | 10/1979 | Japan | 204/301 |

Primary Examiner—John F. Niebling
Assistant Examiner—Terryence Chapman
Attorney, Agent, or Firm—Norman E. Saliba

[57] ABSTRACT

Process and apparatus are described for recovering components sorbed on a body of wet granules that are highly selective for the sorption of said components. The process comprises passing a direct electric current through said body of granules and an ion-permeable substantially hydraulically impermeable barrier juxtaposed with said body of granules in a direction substantially parallel to the smallest dimension of said barrier, thereby facilitating the desorption of at least one of said selected components from said granules. The desorbed components are then separated from said body of granules.

18 Claims, 2 Drawing Figures

PROCESS AND APPARATUS FOR ELECTRICALLY DESORBING COMPONENTS SELECTIVELY SORBED ON GRANULES

BACKGROUND OF THE INVENTION

1. Field of the Invention

Affinity chromatography has become a valuable tool for separating biological materials, for example biologically active molecules such as small ligands, proteins, nucleic acids, enzymes, etc. In affinity chromatography, a substrate is immobilized on a granular support during the chromatography. By utilizing a column of said granular immobilized substrate, materials having affinity or binding specificity for the compounds bonded to the stationary phase can be separated from other materials in a mixture.

Typically, complex polysaccharide granules such as agarose beads, etc. are employed in affinity chromatography. The material of the granules may inherently have the desired sorption specificity or a suitable ligand may be bonded, often through so-called spacer-arms, to the granules by a variety of methods. Components in an ambient solution which have a high binding affinity for the materials of the granules or for the ligand will be preferentially bound to the granules. The bound components may be subsequently removed from the granules by contacting the latter with reagents which dissolve the bond between the component and the material of the granules, or its immobilized ligand. Typically, such desorption is accomplished by a substantial change in pH or ionic strength. Alternately the sorbed component may be desorbed by another ligate which competes for the binding sites. Often chaotropic agents are used which by altering the secondary structure of the sorbed component effect desorption. Examples of specific ligands are:

Lectin absorbents for binding glycoproteins, glycolipids, polysaccharides, and related substances;

Protein A from Staphylococcus aureus for binding many immunoglobulins;

Cibacron ® Blue F3G-A for binding albumin, interferons, growth factors, kinases and dehydrogenases;

Monoclonal antibodies for binding biospecific antigens;

Biospecific antigens for binding monoclonal antibodies; and

Hydrophobic groups (e.g. aliphatic or aromatic moieties) for binding proteins having hydrophobic regions.

Desorption of tightly bound, high molecular weight ligates is generally a rather slow process, and may result in alterations in biological activity of the ligate or loss of biospecificity of the ligands when accomplished by substantial changes in pH, ionic strength or high concentrations of chaotropic reagents.

It is an object of the present invention to provide processes and apparatuses which enable the comparatively rapid and economic recovery of bioactive ligates under comparatively gentle desorption conditions, thereby preserving a substantial fraction of the bioactivity.

These and other objects will become apparent from the following description of the invention.

2. Description of the Prior Art (A) P.J. Brown et al (FEBS Letters, Vol. 83, No. 2, November 1977 pp. 256-259) describe the absorption of antigen ligates on columns of granules having antibody ligands. Electrodes were subsequently placed at the top and bottom of the columns and a direct current passed for about one hour to remove the antigen by electrophoresis. The bioactivity of the recovered antigen was not reported. The electric current passed in a direction substantially parallel to the flow of solution.

(B) M.R.A. Morgan et al (J. Immun. Methods 23 (1978) pp. 381-387) describe sorbtion of immunoglobulin ligates in columns of beads in which the ligands were antisera to the immunoglobulins or Protein A from S aureus. The beads were placed on top of polyacrylamide disc gels. A direct current potential of 50 volts was applied for 4 to 5 hours and the ligates removed by electrophoresis into the disc gels. The bioactivity of the recovered sorbate was not reported.

(C) M.J. Igbal et al (FEBS Letters, Vol. 87, No. 2, March 1978, pp. 235-238) describe sorption of a hormone binding globulin by stirring with beads having ligands of androstanediol. The beads were transferred to a column having electrodes at either end. A direct current potential of 110 volts was applied for 5 hours which resulted in removal of the ligate. Substantial denaturation of the recovered ligate was reported.

(D) M.R.A. Morgan et al (Analyt. Biochem. 105, pp. 1-5, 1980) describe the sorption of albumin in columns of beads having ligands of Cibacron ® Blue F3G-A. The beads were subsequently placed on top of a column of polyacrylamide gel. Direct electric current was passed between electrodes located at the top and bottom of the column. The albumin was eluted electrophoretically into the gel. Elution times required to obtain substantial recoveries of albumin were 10 to 20 hours. The degree of denaturation of the albumin was not reported.

(E) U.S. patent application Ser. No. 675,057, still pending, filed Nov. 26, 1984 entitled "Process and Apparatus for Electrolytically Desorbing Components Selectively Sorbed on Electrolytically Conducting Barriers", which is assigned to the same assignee as this patent application, discloses processes and apparatus for recovering components dispersed in an aqueous solution comprising contacting said solution as a first solution with an electrically conducting barrier which has a high affinity for one of said components. The barrier is subsequently contacted with a second aqueous solution and a direct electric current is passed through said barriers in a direction substantially perpendicular to the barrier and to the flow of solution thereby resulting in the substantial desorption of the sorbed component. Said application does not disclose recovering components sorbed on a body of particulate material such as wet granules that are highly selective for the sorption of said components. The present application comprises the process of passing a direct electric current through said body of granules and an ion-permeable, substantially hydraulically impermeable barrier positioned juxtaposed to said body of granules. The current is passed in a direction substantially parallel to the smallest dimension of said barrier, thereby facilitating the desorption of at least one of said selected components from said granules and separating the desorbed components from said body.

DESCRIPTION OF PREFERRED ENBODIMENTS

In its broadest aspect, the apparatus of the present invention consists of a body of biospecifically sorbed microporous granules juxtaposed to at least one barrier in the shape of an electrolytically conducting substantially hydraulically impermeable film, membrane or diaphragm (which may or may not have specific sorbing properties on at least one major surface) such barrier(s) and granules positioned between a pair of electrodes. Either or both of the electrodes may be in contact with the barriers(s) and or the granules. There may be an array of several such electrolytically conducting, substantially hydraulically impermeable barriers between the pair of electrodes defining solution compartments between the barriers at least some of said compartments being substantially filled with biospecifically sorbed granules.

Figure 1:
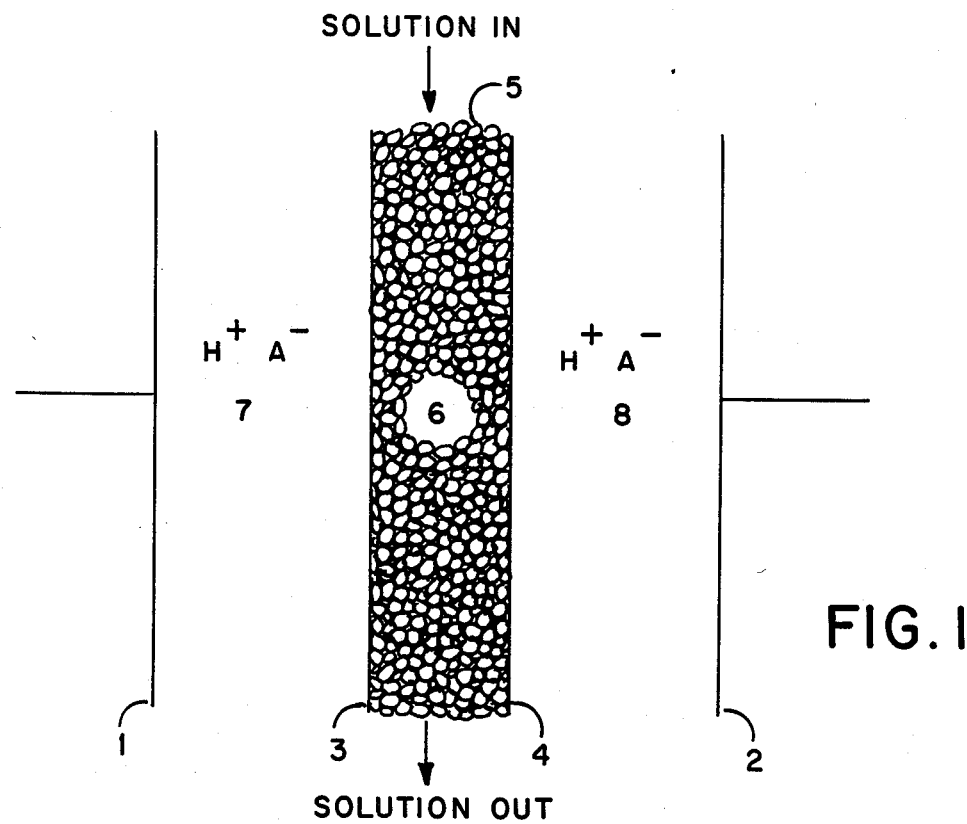
FIG. 1 is a schematic representation of one embodiment of an apparatus having biospecific sorbed granules juxtaposed against at least one electrolytically conducting ion-permeable, substantially hydraulic impermeable barrier (which may also be biospecifically absorbing) in acccordance with the present invention.

Referring to FIG. 1 there is indicated a three-compartment electrolytic cell having a pair of electrodes 1 and 2, a electrolytically conducting barrier 3 juxtaposed with biospecifially sorbed granules 5 on at least one surface. There is also indicated an optional second electrolytically conducting barrier 4 positioned to protect the sorbed granules 5 and/or ligands sorbed thereon or desorbed therefrom from the products of electrolysis at electrode 2. It will be understood that if the sorbing groups and the ligands sorbed thereon are not sensitive to the electrolysis products of electrode 2 then barrier 4 may be eliminated, in which case the granules may be in contact with electrode 2.

Barrier 3 may comprise an inherently electrolytically conducting substantially hydraulically impermeable material such as an ion exchange resin in the form of sheets or films; hydrous material such as a hydrated gel; or a microporous material containing water or an aqueous solution in the pores. Examples of suitable hydrous material are agarose gels, zein, collagen and polyacrylamide gels in the form of sheets. Other suitable hydrous gels will be obvious to those skilled in the art. The sheets are preferably reinforced with woven or nonwoven fabrics to improve the mechanical strength and handling properties.

Examples of suitable micro porous materials are films of Cuprophan ® regenerated cellulose, cellulose acetate and nylon; or inorganic diaphragms such as ceramic diaphragms, all generally having average pore sizes less than about 10 micrometers which inhibit convective mixing of liquids though the barrier.

Optionally the barrier may also have biospecific sorbent properties in which case its composition will ideally be similar to that of the biospecific sorbing granules with which it is in contact. It will be understood that the barrier and granules may have different composition and even different biospecific sorbent properties as long as the differences are compatible with respect to the desired separation.

The granular material 5, generally in contact with barrier 3, (optionally with electrode 1) may have biospecific sorbent properties as in the case of zein, collagen and gels containing transition metal chelates; or biospecific ligand may subsequently be added to the accessible surface. Such ligands may be more or less permanently sorbed on the granular material as for example, certain antibodies can be sorbed on the available surfaces of zein or collagen granules by incubating the latter for prolonged periods in a dispersion of the former. It appears that secondary bonds (that were previously formed between the substrate protein molecules) form between the antibody and the substrate. On the other hand the granular material may be activated in various ways known in the art, for example with cyanogen bromide, trichloro-s-triazine, isocyanate, glutaraldehyde and the like as appropriate to the granular material and the desired ligand. As a third alternative, the granular material may inherently contain active moieties such as granules which are terpolymers of methacrylamide, allyl-glycidyl-ether and N-methylene-bismethacrylamide. Suitable activating agents or active moieties are well-known in the art. The ligands may be bound directly to the accessible granular surface or through leashes, tethers, spacer-arms or other stand-offs depending primarily on the size of the ligand or the target ligate. Suitable stand-offs are well known in the art.

Preferred ligands show a high structural selectivity for the desired ligate and also possess second functional sites at which immobilization to the accessible granular surface may be affected without substantially affecting ligate binding. Depending on the target ligate, a wide variety of ligands may be used. The following table illustrates the various classes, but is not intended to limit the scope of this invention.

| Target Ligate | Suitable Ligand |
| --- | --- |
| 1. Enzymes, apoenzymes | Inhibitor, cofactor, prosthetic group, polymeric substrate |
| 2. Polymeric Inhibitors | Enzymes |
| 3. Nucleic acid, single strand | Nucleic acid complementary strand |
| 4. Antibody | Hapten, antigen |
| 5. Proteins, polysaccharides | Antibody |
| 6. Lectins, receptors | Monosaccharide, polysaccharide |
| 7. Glycoproteins, receptors | Lectin |
| 8. Binding proteins | Small target compounds |
| 9. Small target compounds | Binding protein |
| 10. Trypsin, thrombin, urokinase | Aminobenzamidine |
| 11. Nicotine adenine dinucleotide dependent dehydrogenases | 5'-adenosine monophosphate |
| 12. Immunoglobulin G | S. aureus Protein A |
| 13. Albumin, coagulation factors, interferon | Cibacron ® Blue F3G-A |
| 14. Serum protein, interferon | Chelated transition metals |
| 15. Lactalbumin, catalase ferritin, cytochrome C | Octyl or phenyl moieties |

A preferred method of using the above described apparatus is as follows:

The aqueous solution or suspension containing the target molecules is passed or recirculated through the body of biospecific granules either within the apparatus of this invention or external thereto. In the latter case the sorbed granules are subsequently loaded into the apparatus.

Preferably the thickness of the body of granules as loaded in the apparatus, for example the distance between the barrier 3 and the adjacent protective barrier 4 (or to the adjacent electrode 2 if the protective barrier 4 is not required) is in the range of from about 5 times to about 50 times the average diameter of the granules.

Preferably the thickness of such body in the apparatus is substantially less than the width or length of the body.

When the biospecific capacity of the granules has been substantially saturated and/or the ligate containing solution or suspension has been substantially depleted of target ligate(s), the solution or suspension is withdrawn from further contact with the body of granules and the latter rinsed with pure water or other appropriate aqueous solutions to remove traces of the ligate containing solution or suspension and/or to remove non-specifically sorbed components from the granules. If the sorption step was carried out external to the apparatus, the sorbed granules are then loaded into the apparatus. The apparatus is then ready for desorption of one or more of the sorbed ligates with the facilitation of a direct electric current.

Several desorption modes are contemplated. One of these may be described with reference to FIG. 1 in which 5 represents a body of biospecific granules in contact with the barrier 3 and the barrier 4, 7 represents a compartment defined between the barrier 3 and the electrode 1 (or in the case where several barriers are arranged between a single pair of electrodes, the compartment defined between the barrier 3 and another barrier generally similar in properties to barrier 3). In the embodiment of this invention represented in FIG. 1, compartment 7 is filled with an appropriate acid solution which may be, for example, a dilute solution of a strong acid, a weak acid or of an acidic buffer. Compartment 6 is filled with or wet with an appropriate liquid, the choice depending on both the ligand(s) and the ligate(s), generally a buffer solution or pure water. Electrode 1 is made anodic and electrode 2 cathodic causing the transport of hydrogen ions across barrier 3 (which is preferable cation-selective or non-selective) into the granules in compartment 6. In a preferred method of operation, the electric current is continued for a period sufficient to reduce the pH in the body of granules to a value at which the ligate-ligand complexes dissociate and the ligate begins to diffuse away from the granules into the liquid remaining in the compartment 6. According to such preferred method, the liquid in compartment 6 is not flowing during the period in which the electric current flows. It will be understood that the interstices in the bed of granules or other particulate material need not be filled with liquid if the moist granules (for example containing sorbed liquid) are electrolytically conducting. Again in accordance with said method, after the flow of electric current ceases (or is reduced to a maintenance value), the diffusion of the dissociated ligate(s) into the liquid is allowed to continue for some minutes before the contents of compartment 6 are removed. The duration of such diffusion period depends on the diffusion constant(s) of the ligate(s) (and therefore generally on the molecular weight) but is generally sufficiently long to permit a substantial fraction of the ligate to diffuse out of the granules. Compartment 6 is then drained or rinsed, preferably by imposing a flow of liquid through the compartment. In this way the first compartment volume of liquid issuing from compartment 6 will contain a substantial fraction of the dissociated ligate at a comparatively high concentration.

It will be seen that by this method, particularly if the thickness of the body of granules is substantially less than the width or length of that body, the dissociating reagent is applied rapidly to the biospecific granules and the dissociated ligate(s) (and ligand) is (are) exposed to the dissociating entity for only a short period of time compared with the conventional affinity chromatography methods using granules. It is found therefore that the dissociating conditions are particularly gentle and comparatively little denaturation of the ligate occurs, resulting in higher recoveries (yields) of bioactivity.

The operation of the apparatus of FIG. 1 has been described by reference to effecting an alteration in pH in the biospecific granules. Alternatively, compartment 7 may contain a chaotropic agent such as guanidine hydrochloride in which ease guanidinium cations will be transferred across the barrier (which should then not be anion-selective) to the biospecific granules resulting in dissociation of the ligate(s). Subsequent steps in the operation will be substantially as described above. Dissociation may also be effected by causing a substantial change in the ionic strength in the biospecific granules by passage of electric current. This is particularly effective and efficient when the barrier 3 is ion selective, for example when it comprises an ion exchange resin. If the ligate will be dissociated by an increase in ionic strength and if the barrier 3 is cation selective, then electrode 1 should be anodic and electrode 2 cathodic. It will be obvious to those skilled in the art that if barrier 3 is anion selective then electrode 1 should be cathodic and electrode 2 anodic. On the other hand if the ligate will be dissociated by a decrease in ionic strength (as, for example, when the ligands are hydrophobic groups) and if the barrier 3 is cation selective then electrode 1 should be cathodic and electrode 2 anodic. It will be obvious that if the barrier 3 is instead anion selective, the potential of the electrodes must be reversed.

If dissociation of the ligate(s) is effected by an electrically controlled change in ionic strength as described above and if the barrier 3 is ion selective then it may be advantageous if the barrier 4 has the opposite ionselectivity, i.e. if barrier 3 is cation-selective then barrier 4 may be advantageously anion-selective.

Depending upon the composition of the liquids in compartments 6, 7, and 8, the heat generated by the applied current may be excessive in which case the contents of compartments 7 and 8 may be advantageously recirculated through an external heat exchanger, absorbing heat from compartment 6 through barriers 3 and 4.

Referring again to FIG. 1, the transfer of the dissociating agent may be continued through only one barrier until the pH, ionic strength or concentration of chaotropic agent is sufficient throughout the body of granules to result in dissociation of the ligate(s) from the ligand(s). After an appropriate interval the contents of compartment 6 are flushed out.

Alternatively the dissociating agent may first be transferred from compartment 7 at least halfway through the body of biospecific granules in compartment 6 and after an appropriate interval (with or without passage of a maintenance current) the contents of compartment 6 are swept out. The polarity of the electric current may subsequently be reversed and the dissociating agent (generally the same one used in the prior step) transferred electrically from compartment 8 again at least halfway through the body of biospecific granules 5 and after an appropriate interval the contents of compartments 6 again swept out. Such step-wise procedure can provide a particularly gentle dissociating environment.

In another embodiment, one of barriers 3 and 4 is ion selective and the other has alternatively no ion selectively, substantially less selectively of the same sign or has selectivity of the opposite sign. In such case the direction of the applied electric current is such as to increase the ionics strength in compartment 6 if the ligate will be dissociated by such an increase. On the other hand if the ligate will be dissociated by a decrease in ionic strength, then the direction of the electric current should be such as to decrease the ionic strength in compartment 6.

Figure 2:
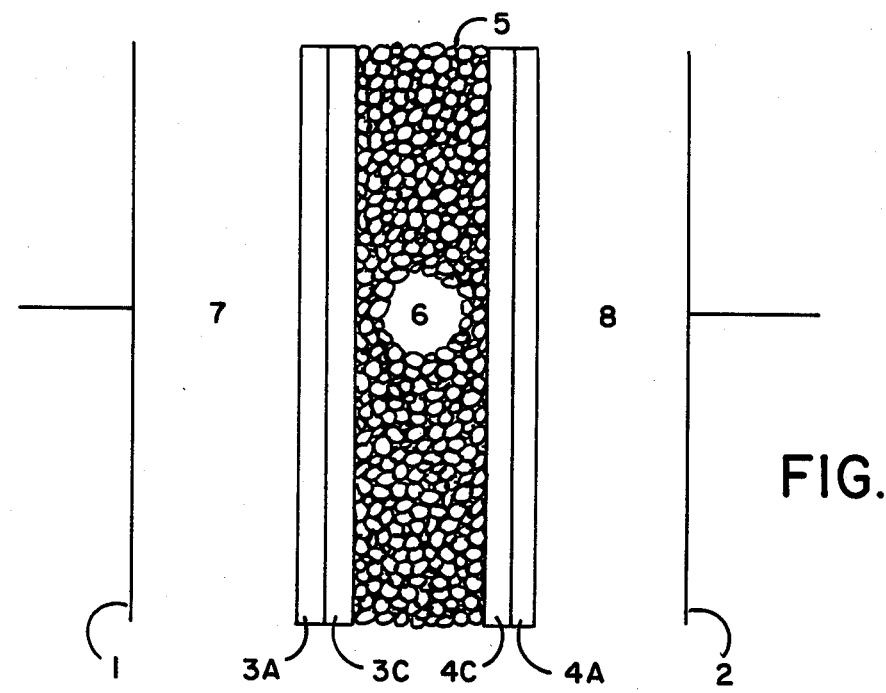
FIG. 2 is a schematic representation of a second embodiment of an apparatus having water-splitting electrolytically conducting barriers and biospecific sorbed granules in accordance with the present invention.

Yet another embodiment of the invention may be described with respect to FIG. 2 in which either or both of the barriers 3 and 4 are bipolar ion selective membranes (for example as described in U.S. Pat. No. 3,562,139-Leitz). For example regions 3a and 4a may comprise anion selective material and regions 3c and 4c may comprise cation selective material. When electrode 1 is made anodic and electrode 2 cathodic, the interface between regions 3a and 3c, rapidly becomes substantially depleted of electrolyte. If passage of electric current is thereafter continued it will be carried through region 3a by hydroxide ions resulting from the dissociation of water at or near the interface between regions 3a and 3c. Current through region 3c will be carried by hydrogen ions (resulting from such water dissociation) at least half way through the body of biospecific granules in compartment 6 resulting in dissociation of ligate-ligand complexes. After an appropriate interval, the contents of compartments will be swept out together with the dissociated ligate. The direction of the electric current may then if desired, be reversed causing hydrogen ions generated at the interface between regions 4a and 4c to dissociate ligand-ligate complexes at least in the biospecific granules in the region adjacent to barrier 4. After an appropriate interval the contents of compartment 6 are again swept out.

It can be appreciated that if a single pass of the liquid through one apparatus as described above does not absorb the required amount of the component of interest, a series of apparatuses can be arranged in which the liquid flows in series through each, with each adsorbing a portion of the said component. Each apparatus may instead contain two or more hydraulic stages between electrodes as is well known in the electrodialysis art. Alternatively, a single stage unit can be employed by which the liquid is continuouly recirculated therein in a batch mode until the required adsorption is attained. The number of compartments in each electrical stage and the number of stages in series can of course be varied depending upon the particular application and production rate required.

If more than one absorption stage is used in series or in parallel then it may be appropriate to stage also the desorption step, preferably countercurrently and in series. For example the ligate in the last absorption stage may be dissociated first and the liquid contents of compartment(s) 6 in such stage sent to compartment(s) 6 in the next prior absorption stage after which the ligate is such stage is dissociated. The procedure is repeated stage by stage countercurrently, thereby building up the concentration of recovered ligate in a small volume of liquid.

Although the process and apparatus of this invention have been described for the sake of simplicity in terms of barriers and electrodes which are planar, flat sheets, it will be understood that other configurations may be advantageously used. For example, referring again to FIG. 1, the electrodes and barriers may be arranged as concentric cylinders, in which case the central electrode may have the form of a rod or wire.

The following non-limiting examples illustrate the invention:

EXAMPLE 1

A 3-compartment apparatus is constructed in accordance with FIG. 1. Barrier 3 is a CR61 AZL cation selective membrane and barrier 4 an AR204 SXZL anion selective membrane, both membranes available from Ionics, Incorporated, Watertown, Mass., U.S.A. The barriers are arranged vertically and have dimensions of about 15.2 by 7.6 cm and are about 0.06 cm thick reinforced with a fabric woven from spun, modacrylic staple. The electrodes are platinized titanium of the same dimensions. The electrodes are separated from the barriers by open spacers fabricated from low density polyethylene and having a thickness of about 0.1 cm and an effective area of about 15 cm. The barriers are separated from each other by a composite of five similar spacers, i.e. the distance between the barriers is about 0.5 cm. The effluent channels from such central compartment spacer are at the bottom of the vertically oriented spacer and separated from the working area by a strip of modacrylic filter cloth fastened to the spacer.

About 7.5 milliliters of wet agarose acrylamide copolymer hydrous gel beads containing a high density of L-lysine groups coupled to the beads by cyanogen bromide are rinsed with about 0.1 molar sodium hydrogen phosphate buffer having a pH of about 7.4. Twenty ml. of human blood plasma are diluted 1:1 with distilled water and contacted with the beads. The solution is removed from contact with the beads and the latter are rinsed with 0.3 M sodium hydrogen phosphate buffer having a pH of about 7.4 and then flushed by said buffer into the central compartment of the above electrodialysis apparatus, the beads being retained by the filter cloth until the compartment is essentially filled with beads. The buffer is drained from the compartment. A 0.3 molar solution of epsilon-aminocaproic acid adjusted to a pH of about 11 with sodium hydroxide is circulated through the cathode compartment and 0.3 M epsilon-aminocaproic acid solution adjusted to a pH of about 4.5 with hydrochloric acid is circulated through the anode compartment. A current of about one ampere is passed for a few minutes. The contents of the center compartment 6 are flushed out immediately or after waiting a few minutes and are found to contain about 100 micrograms of plasminogen.

The beads are subsequently removed from the center compartment by back flushing and are recovered.

EXAMPLE 2

A 3-compartment apparatus is constructed in accordance with FIG. 1. Barriers 3 and 4 are CR61 AZL cation selective membranes available from Ionics, Incorporated, Watertown, Mass. U.S.A. The barriers are arranged vertically and have dimensions of about 15.2 by 7.6 cm and are about 0.06 cm thick, reinforced with fabric woven from spun, modacrylic staple. The electrodes are platinized titanium of the same dimensions. The electrodes are separated from the barriers by open spacers fabricated from silicone rubber and having a thickness of about 0.1 cm and an effective area of about 15 cm. The barriers are separated from each other by a composite of five similar spacers, i.e. the distance between the barriers is about 0.5 cm. The effluent channels from the central compartment spacer are at the bottom of the vertically oriented spacer and separated from the working area by a strip of filter cloth affixed to the spacer. An aqueous slurry of agarose gel beads which have been activated serially with dusopropylethylamine, trichloro -s- triazine and aniline in dioxane (as well known in the art) is flowed into the central compartment, the beads being retained by the filter cloth, until the compartment is essentially filled with beads. The body of agarose beads is rinsed with an aqueous solution about 0.1 molar in sodium hydrogen phosphate, 0.1 molar in sodium chloride and having a pH of about 8.6. A solution of monoclonal anti-Hepatitis-B-Surface-Antigen-IgM having about 1 milligram of antibody per milliliter of solution is circulated through the central compartment at about 4° C. for about 24 hours. This solution is also about 0.1 molar in sodium hydrogen phosphate about 0.1 molar in sodium chloride and has a pH of about 8.6. The solution is subsequently drained and the compartment rinsed with the phosphate/chloride buffer solution. Hepatitis B Surface Antigen positive serum diluted with phosphate buffered saline containing 1% bovine serum albumin and having about 40 micrograms of antigen per milliliter is recirculated through the central compartment. The antigen solution is drained and the compartment rinsed with phosphate/chloride buffer and then filled with fresh buffer solution. A 0.05 molar glycine HCl solution (pH 2.2) is circulated through compartment 7 (the anode compartment in this case) and phosphate/saline buffer through the cathode compartment (compartment 8 in this case). A current of about one ampere is passed for several minutes and the contents of the central compartment are then flushed out with phosphate/chloride buffer. The recovered antigen is found to be immune reactive.

EXAMPLE 3

A 3-compartment apparatus is constructed in accordance with FIG. 1 and Example 2. Barrier 3 is prepared from Cuprophane ® dialysis membrane having dimensions of about 15.2 by 7.6 cm. The sheet is activated with tosyl chloride and then mounted in the apparatus of Example 2 as Barrier 3. Barrier 4 is a CR61 CZL cation selective membrane as in Example 2. An aqueous slurry of agarose gel beads which have been activated with tosyl chloride are flushed into the central compartment with water, the beads being retained by the filter cloth, until the compartment is essentially filled with beads. The central compartment is rinsed with phosphate/chloride buffer and then a solution of antiFactor VIII c in phosphate/chloride buffer is recirculated through the central compartment for about 24 hours at about 4° C. The compartment is drained and rinsed with buffer solution. Cryoprecipitate from human blood plasma is dissolved in phosphate/chloride buffer to give a solution having about 20 milligrams of protein per milliliter. The solution is recirculated through the central compartment. The partially depleted cryoprecipitate solution is drained from the compartment which is then rinsed with fresh buffer. An approximately 3 molar solution of sodium thiocyanate of about pH 7 is recirculated through compartments 7 and 8. Electrode 1 is made cathodic and electrode 2 anodic. A current of about 1 ampere is passed for several minutes. Thereafter the contents of the central compartment are rapidly flushed out with buffer solution and immediately dialyzed to reduce the concentration of chaotropic agent as rapidly as possible. The recovered desorbate is found to contain undenatured FVIII.

EXAMPLE 4

A 3-compartment apparatus is constructed in accordance with FIG. 1 and Example 2. Barrier 3 is an anion-selective membrane having a macroreticular surface prepared in accordance with the teachings of U.S. Pat. Nos. 3,749,655 and 3,926,864 from divinyl benzene and vinyl benzyl chloride. The macroreticular surface is treated with an aqueous solution of N, N dimethyl ethanolamine and subsequently the entire membrane is treated with an aqueous solution of trimethyl amine. The macroeticular surface is next treated with bisepoxirane and subsequently with normal octyl alcohol to introduce hydrophobic octyl groups into the macroreticular surface. A piece of said membrane approximately 15.2 by 7.6 cm and having a thickness of about 0.06 cm is mounted in the apparatus of Example 2 as Barrier 3 with the macroreticular surface facing the central compartment. Barrier 4 is a CR61 CZL cation selective membrane as in Example 2.

Macroreticular granules are prepared from divinyl benzene and vinyl benzyl chloride and treated sequentially as described above with dimethyl ethanol amine, trimethylamine, bisepoxirane and n-octanol. The granules are flushed into the central compartment of the electrodialysis cell with water, the granules (beads) being retained by the filter cloth, until the compartment is essentially filled with granules.

The central compartment is rinsed with 1 molar ammonium sulfate. A solution having about 1 milligram of catalase (asperigillus niger) per milliliter of 1 molar ammonium sulfate is circulated through the central compartment which is subsequently drained and rinsed with 1 molar ammonium sulfate. The compartment is filled with a solution one molar in ammonium sulfate and 4 molar in urea. A solution of 0.1 molar ammonium sulfate is circulated through compartments 7 and 8. Electrode 1 is made anodic and electrode 2 cathodic. A potential of about 10 volts is maintained across the electrodes. The initial current decreases rapidly and when after several minutes it reaches a steady state value, the contents of the central compartment are flushed out, and dialyzed rapidly to reduce the concentration of urea. It is found that the desorbate contains active catalase.

For purposes of this invention the term "granules" as used herein is intended in its broadest aspect to mean a particulate material of various shapes such as spherical, cylindrical, fibrous (ribbon or thread shaped) or the like. It is also intended that in place of the individual granules or particles that make up the porous body or packed bed material filling a compartment; there could be substituted therein a porous body having a foamed, expanded, screened, woven, knitted, matted or felt like structure.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent assemblies and methods.

What is claimed is:

1. A method of recovering biospecifically, sorbable components sorbed on a body of granules having biospecific sorbing properties for said components comprising:

(a) passing a direct electric current through said body of granules in a direction substantially parallel to the smallest dimension of said body, thereby facilitating the desorption of at least one of said components having biospecific binding affinity for the said granules; and (b) removing said desorbed components from contact with said granules.

2. The method according to claim 1 wherein said granules consist of a particulate material selected from the group of spherical, cylindrical, fibrous, foamed, expanded, screened, woven, knitted, matted or felt like structures.

3. A method for recovering biospecifically, sorbable components sorbed on a body of granules having biospecific sorbing properties for said components comprising:

(a) passing a direct electric current through said body of granules and an ion-permeable barrier juxtaposed with said body of granules in a direction substantially parallel to the smallest dimension of said barrier, thereby facilitating the desorption of at least one of said components having biospecific sorbing properties for said granules; and (b) removing said desorbed components from contact with said granules.

4. The method according to claim 3 wherein said granules consists of a particulate material selected from the group of sphherical, cylindrical, fibrous, foamed, expanded, screened, woven, knitted, matted or felt like structures.

5. A method of recovering biospecifically, sorbable components dispersed in aqueous solution comprising:

(a) contacting said solution as a first solution with a body of granules having biospecific sorbing properties for at least one of said components whereby a substantial fraction of said components in said solution having biospecific binding affinity for said granules is sorbed by said granules;

(b) removing said first solution from contact with the said granules;

(c) contacting said granules with a second aqueous solution;

(d) passing a direct electric current through said body of granules, through said second solution and through an ion-permeable substantially hydraulically impermeable barrier in contact with said body of granules, in a direction substantially parallel to the smallest dimension of said barrier thereby facilitating the desorption of at least one of said components having biospecific binding affinity for the said granules to said second solution; and (e) removing said second solution from contact with said granules.

6. The method according to claim 5 wherein said granules consists of a particulate material selected from the group of spherical, cylindrical, fibrous, foamed, expanded, screened, woven, knitted, matted or felt like structures.

7. Apparatus for recovering biospecifically, sorbable components sorbed on a body of granules having biospecifically sorbing properties for said components comprising:

(a) said body of granules having biospecific sorbing properties and means for passing a direct electric current through said body of granules in a direction substantially parallel to the smallest dimension of said body, thereby to facilitate the desorption of at least one of said components having biospecific binding affinity for the said granules; and (b) means for removing said desorbed components from contact with said granules.

8. Apparatus according to claim 7 wherein said granules consists of a particulate material selected from the group of spherical, cylindrical, fibrous, foamed, expanded, screened, woven, knitted, matted or felt like structures.

9. Apparatus for recovering biospecifically, sorbable components sorbed on a body of granules having biospecific sorbing properties for said components comprising:

(a) an electrolytically conducting, substantially hydraulically impermeable barrier juxtaposed to said body of granules;

(b) means for contacting said body with an aqueous receiving solution;

(c) means for passing a direct electric current through said barrier and said body in a direction substantially parallel to the smallest dimension of said barrier, thereby to facilitate the desorption of at least one of said components having biospecific binding affinity for the said body; and (d) means for removing said aqueous receiving solution from contact with said body.

10. Apparatus according to claim 9 in which said barrier has the form of a cylinder.

11. Apparatus according to claim 9 in which said barrier has the form of a spiral.

12. Apparatus according to claim 9 in which said granules contain ligands selected from the group consisting of enzyme inhibitors, enzyme substrate analogues, coenzymes, apoenzyme polymeric substrates, enzymes, nucleic acid complementary strands, haptens, antibodies, monosaccharides, polysaccharides, lectins, small target compounds for binding proteins, binding proteins, amino-benzamidine, 5' adenosine monophosphate, *S. aureus* Protein A, hormones, hormone receptors, and immobilized textile dyes.

13. Apparatus according to claim 9 in which said barrier is selected from the group consisting of non-selective membranes, sheets of hydrous gels and porous sheets having average pore sizes of less than about 10 micrometers.

14. Apparatus according to claim 9 in which said barrier is a macroreticular ion-selective membrane.

15. Apparatus according to claim 9 in which said barrier is an ion-selective membrane.

16. Apparatus according to claim 9 in which said barrier is a bipolar ion selective membrane.

17. Apparatus according to claim 9 in which said barrier is an ion-selective membrane having ligands attached to a macroeticular surface.

18. Apparatus according to claim 9 in which said granules consist of a particulate material selected from spherical, cylindrical, fibrous, foamed, expanded, screened, woven, knitted, matted or felt like structures.

* * * * *